United States Patent [19]
Pernicka

[11] Patent Number: 5,963,295
[45] Date of Patent: Oct. 5, 1999

[54] PROTECTIVE EYEGLASS ASSEMBLY FOR USE DURING SPORT ACTIVITIES

[75] Inventor: Martin Pernicka, Laval, Canada

[73] Assignee: Leader Industries Inc., Quebec, Canada

[21] Appl. No.: 09/127,686

[22] Filed: Jul. 31, 1998

[51] Int. Cl.[6] .................................................. G02C 1/00

[52] U.S. Cl. .............................. 351/83; 351/86; 351/124; 2/442

[58] Field of Search ................................ 351/83, 85, 86, 351/124, 129–135; 2/426, 442, 443, 445, 446

[56] References Cited

U.S. PATENT DOCUMENTS

| 2,270,855 | 4/1942 | Bushell | 351/124 |
| 4,056,853 | 11/1977 | Bottazzini et al. | 2/443 |
| 5,642,178 | 6/1997 | Leonardi et al. | 351/111 |

*Primary Examiner*—Huy Mai
*Attorney, Agent, or Firm*—W. Warren Taltavull; Farkas & Manelli PLLC

[57] ABSTRACT

A protective eyeglass assembly for use during sport activities comprises a pair of separate lens frames individually cooperating with a lens holder to secure a pair of lenses therebetween. A detachable nose bridge interconnects the pair of separate lens frames with the lens holder so as to form a unitary eyeglass assembly, easily dismountable for lens replacement due to lens damage or lens prescription.

15 Claims, 4 Drawing Sheets

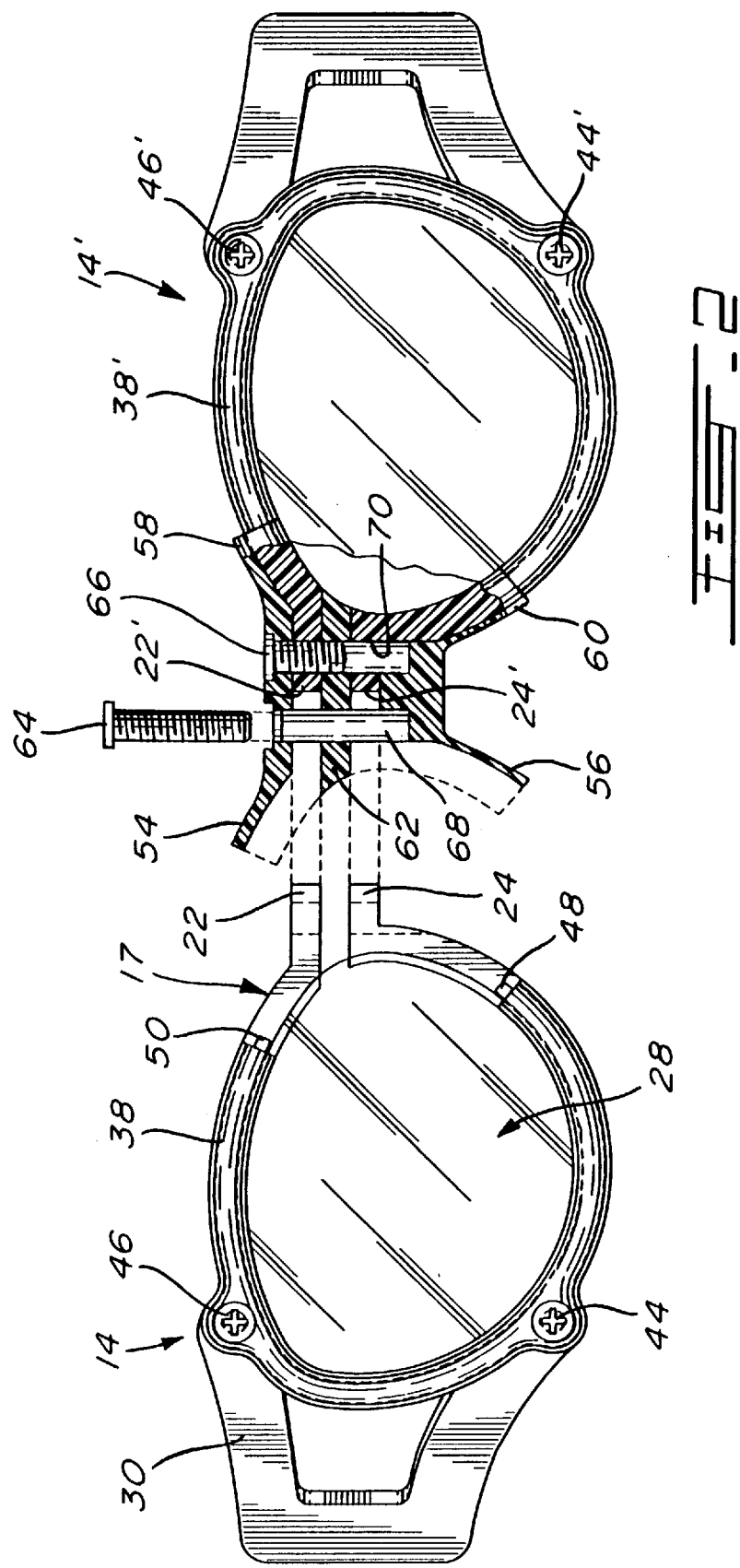

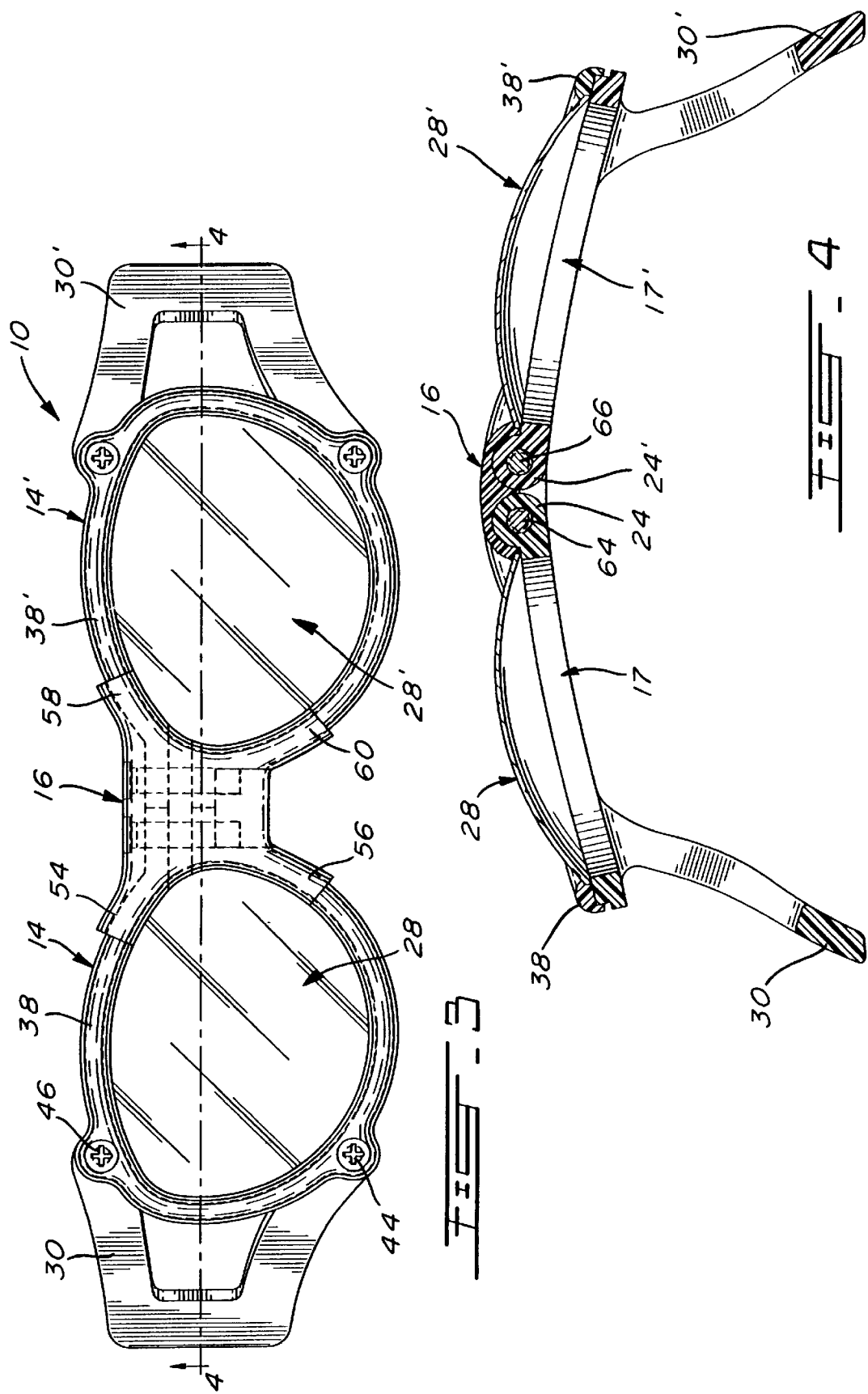

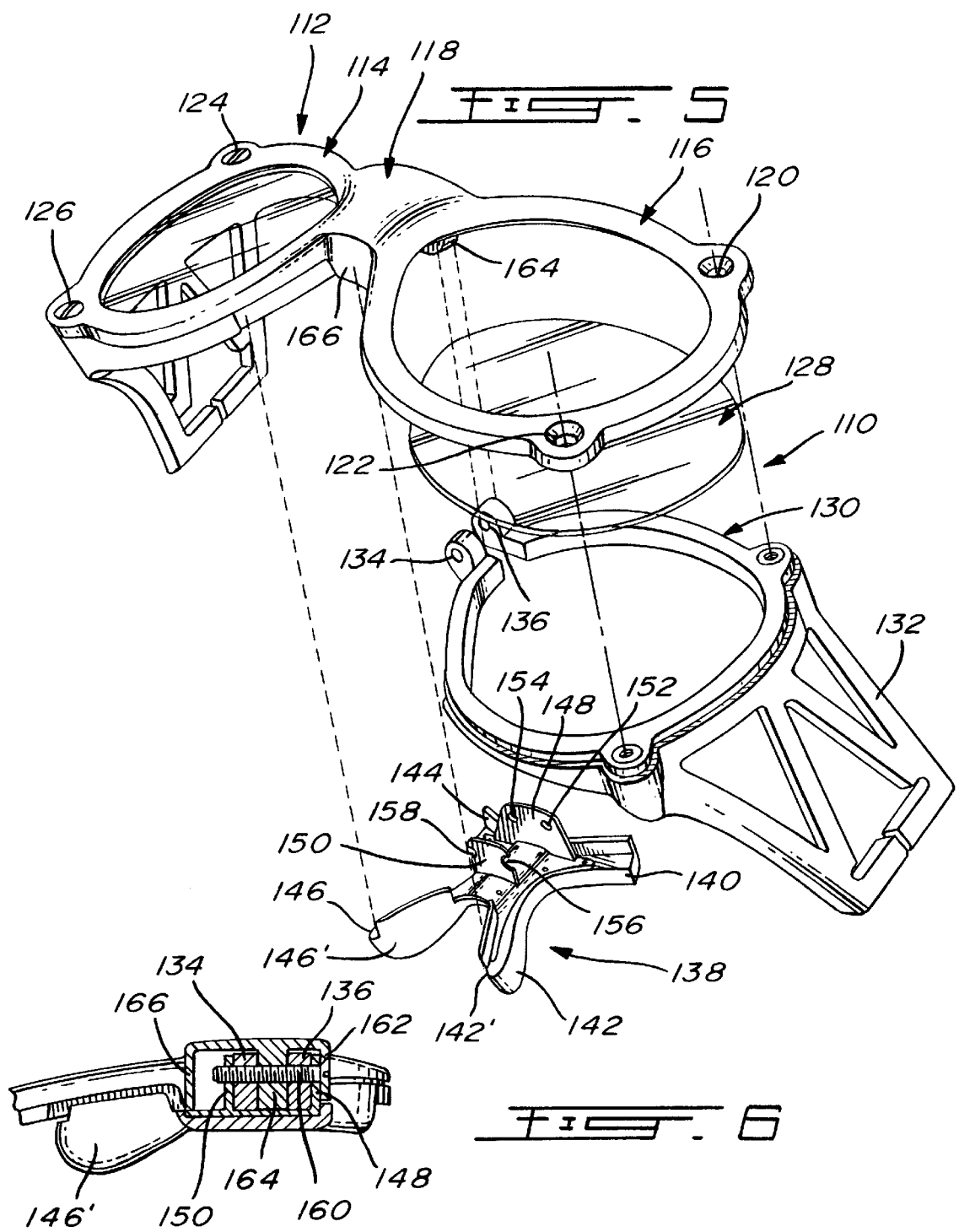

5,963,295

PROTECTIVE EYEGLASS ASSEMBLY FOR USE DURING SPORT ACTIVITIES

FIELD OF THE INVENTION

The present invention relates to a protective eyeglass assembly and, more particularly, to such eyeglasses which are constructed to absorb hard impact which often arise in certain sport activities. The construction of such eyeglass assembly is such that it must be easily dismountable, especially for lens replacement, either due to damage or to lens prescriptions.

BACKGROUND OF THE INVENTION

Various eyeglass assemblies enabling variation or modification of their construction are known. For example, one such eyeglass structure is described in U.S. Pat. No. 5,270,743 issued Dec. 14, 1993 to Hofmair et al. In this eyeglass frame, simple separable coupling means are provided between a common top rim member and a bottom rim member, the coupling being required to reliably lock these members in an engaged position.

While it is possible to replace lenses of standard eyeglasses, it is also important to provide such feature in the more structurally rigid eyeglass assembly used especially during sport activities so that a change in a lens prescription of the user will not result in the buy of a new eyeglass assembly to suit the new prescription.

STATEMENT OF THE INVENTION

It is an object of the present invention to provide in eyeglasses, especially those used in sports, the possibility of replacing lenses for any reasons, such as change in lens prescription, damage, etc.

The present invention pertains to a structurally rigid eyeglass assembly which is demountable so that lens substitution can be made without altering its construction.

The present invention therefore relates to a protective eyeglass assembly which comprises:

a pair of separate lens supporting frames, each frame defining a C-shaped body having free ends;

lens holder means having a shape to fit over the peripheral portions of the lenses;

first fastening means securing the holder means to the frames to tightly secure the lenses therebetween;

nose bridge means detachably mounted to the pair of lens frames and the lens holder means; and second fastening means engaging and securing the free ends of the lens frames and the lens holder means to form a unitary eyeglass assembly, dismountable for lens replacement.

In one form of the invention, the lens holder means consist of a single lens covering component having a pair of lens covering portions and an intermediate nose portion; a nose bridge is affixed to the rear of the nose portion.

In another form of the invention, the lens holder means consist of a pair of separate lens covering components with a nose bridge interconnecting both components.

Other objects and further scope of applicability of the present invention will become apparent from the detailed description given hereinafter. It should be understood, however, that this detailed description, while indicating preferred embodiments of the invention, is given by way of illustration only, since various changes and modifications within the spirit and scope of the invention will become apparent to those skilled in the art.

BRIEF DESCRIPTION OF THE DRAWINGS

FIG. 2 is a front elevational view showing the nose bridge in cross-section;

FIG. 3 is a front elevational view of the assembled eyeglass;

FIG. 4 is a cross-sectional view taken along line 4—4 of FIG. 3;

FIG. 5 is an exploded perspective view of another embodiment of an eyeglass assembly made in accordance with the present invention; and FIG. 6 is a cross-sectional view of the nose portion of the assembly of FIG. 5.

DESCRIPTION OF PREFERRED EMBODIMENTS

Figure 1:
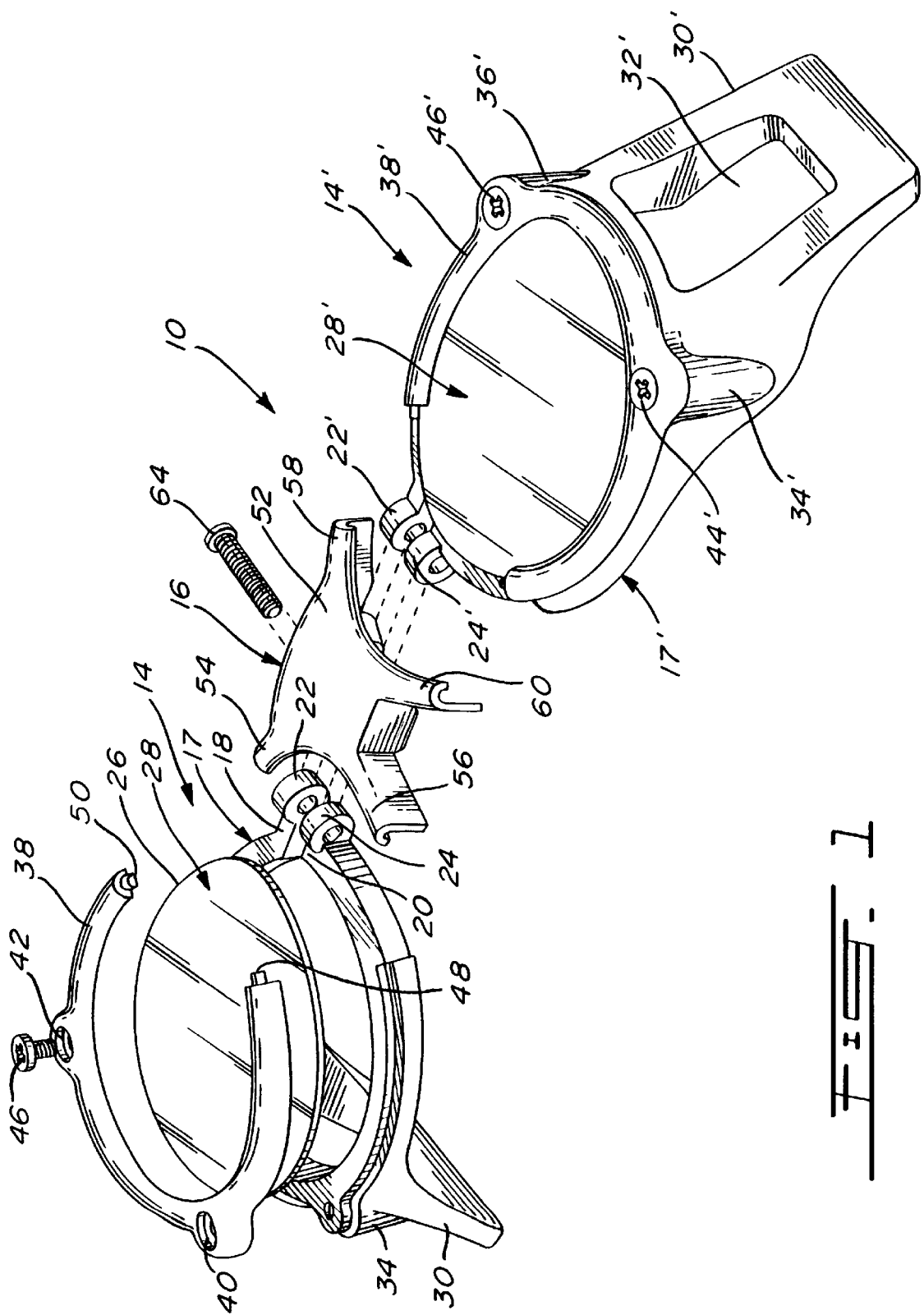
FIG. 1 is an exploded perspective view of one embodiment of an eyeglass assembly made in accordance with the present invention.

Referring to FIG. 1, there is shown a first embodiment of a rigid protective eyeglass assembly, generally denoted 10, adapted to be used by persons engaged in sports, such as racket ball, hand ball or like sport activities where hard impact often occurs.

The assembly comprises a pair of identical individual lens assemblies, generally denoted 14 and 14' interconnected by means of a nose bridge 16. Lens assemblies 14 and 14' being identically constructed, reference will be made to either of them for a description of its construction. The latter comprises a lens frame 17 which has the shape of a C-shaped ring including an interrupted portion defining opposed free ends 18 and 20. These ends terminate in the form of a pair of spaced eyelets 22, 24.

The peripheral edge 26 of a lens 28 rests on the periphery of the lens frame 17.

The lens frame 17 includes a temple extension 30 having such a shape as to follow the temple of a user's head. The extension 30 includes an opening 32 allowing a strap to pass therethrough to secure the eyeglass assembly to the user's head. The lens frame 17 also includes a pair of fastener receiving areas 34 and 36.

The lens assembly also includes a lens holder 38 having a C-shaped body and a pair of fastener receiving openings 40 and 42 that come in registry with the respective fastener receiving openings in the areas 34 and 36 of the lens frame 17. A pair of fasteners 44' and 46' secure the C-shaped body 38' to the lens frame 17' by contacting the peripheral edge 26' of the lens and securing it in the manner illustrated for lens assembly 14' of FIG. 1. The free ends of the C-shaped body 38 have small projections 48 and 50, the function of which will be described further hereinbelow.

The pair of individual lens assemblies of the present embodiment are connected together by means of the nose bridge 16. This nose bridge is formed of a main front portion 52 with opposite pairs of arms 54, 56 and 58, 60. As can be seen in FIG. 2, the underside of the nose bridge has a horizontal central portion 62 which is so shaped as to be lodged between the eyelets 22 and 24 of the lens assembly 14 as well as between the eyelets 22' and 24' of the lens assembly 14'. This central portion 62 has a pair of openings which are adapted to come in registry with the openings of eyelets 22 and 24, 22' and 24' so that a pair of fasteners 64 and 66 may be engagedly secured in a pair of fastener receiving tubes 68 and 70 extending through the eyelets and the nose bridge. As can be seen in FIG. 1, the extremities of arms 54, 56, 58 and 60 define inverted J-shaped configurations in which are lodged the extensions 48 and 50, 48' and 50' of the C-shaped bodies 38 and 38'.

FIGS. 3 and 4 show the eyeglass assembly of FIGS. 1 and 2 in the assembled condition.

Referring to FIGS. 5 and 6, a second embodiment 110 of the present invention is illustrated. A major difference between this embodiment and the embodiment illustrated in FIGS. 1–4 is the construction of the lens holder 112 which is a unitary body (instead of two components as illustrated for the first embodiment) consisting of a pair of opposite lens covering portions 114 and 116 and a nose portion 118 which extends between the two portions 114 and 116. Each lens covering portion comprises a pair of openings (120, 122 for portion 116) to receive fasteners such as 124, 126 shown on portion 114. A pair of lenses (one being shown as 128) are retained between the lens holder 112 and a pair of lens frames (one being shown as 130), which lens frames are identical to the lens frames 14, 14' of the embodiment illustrated in FIGS. 1–4. However, in this embodiment, the strap receiving area 132 has been shown somewhat different in configuration to illustrate that many configurations of strap connecting portions are possible. Lens frame 130 is C-shaped with free ends 134, 136.

A nose bridge 138 is adapted to fit to the rear of the nose portion 118 of the lens holder 112. It comprises four side extensions 140, 142, 144, 146 that cover part of the periphery of the lens frames 130; extensions 142 and 146 have nose contacting surfaces 142' and 146'. A pair of parallel tongues 148 and 150 have openings 152, 154, 156, 158 for receiving fasteners 160 to secure the eyeglass assembly. Nose portion 118 has three parallel horizontal portions 162, 164, 166 integral with the rear face of the nose portion; portions 162 and 164 each have a pair of openings to receive fasteners therethrough. Portion 164 is somewhat thicker than the other two portions to provide rigidity to the connection.

It can be seen that with the protective eyeglass assembly 10 of the present invention, should it be required to change the lenses 28 and 28' of the embodiment illustrated in FIGS. 1–4, this is easily carried out by removing fasteners 44 and 46, 44' and 46' as well as the fasteners 64 and 66 of the nose bridge. Similarly, should it be required to replace the lenses 128 of the embodiment of FIGS. 5 and 6, fasteners 124, 126 and 160 are loosened and a new pair of lenses inserted between the lens frames and the lens covering portions of the lens holder.

To provide rigidity to the eyeglass assembly, the lens frames and the lens holders of both embodiments should be made of a rigid plastic material.

Although the invention has been described above with respect with one specific form, it will be evident to a person skilled in the art that it may be modified and refined in various ways. For example, by modifying the fastener receiving portions of the lens holders and of the lens frames, the fasteners 44, 46 (44', 46') as well as fasteners 124, 126 could be inserted from the rear of the assembly so that their heads would not be seen on the front face of the eye assembly. It is therefore wished to have it understood that the present invention should not be limited in scope, except by the terms of the following claims.

I claim:

1. Protective eyeglass assembly comprising:

a pair of separate lens supporting frames, each frame defining a C-shaped body having free ends; said free ends defining fastening receiving means;

a pair of lenses each having a peripheral portion bearing against said body;

lens holder means having a shape to fit over said peripheral portions of said lenses;

first fastening means securing said lens holder means to said lens frames to tightly secure said lenses therebetween;

nose bridge means defining a pair of fastening receiving means; and second fastening means engaging said fastening receiving means of said ends of said lens frames and said fastening receiving means of said nose bridge means to secure said lens supporting frames to said lens holder means and to form a unitary eyeglass assembly, dismountable for lens replacement.

2. Eyeglass assembly as defined in claim 1, wherein said nose bridge means includes a U-shaped nose contacting lower extension.

3. Eyeglass assembly as defined in claim 1, wherein each said lens frame includes a temple extension.

4. Eyeglass assembly as defined in claim 3, wherein each said temple extension includes means for receiving a strap for securing said assembly to a wearer's head.

5. Protective eyeglass assembly comprising:

a pair of separate lens supporting frames, each frame defining a C-shaped body having free ends, said free ends defining fastening receiving means;

a pair of lenses each having a peripheral portion bearing against said body;

lens holding means having a pair of lens covering portions cooperating with said lens frames to retain said lenses therebetween and an intermediate nose portion extending between said lens covering portions;

first fastening means securing said lens holding means to said lens frames to tightly secure said lenses therebetween;

a nose bridge defining a pair of fastening receiving means; and second fastening means engaging said fastening means of said free ends of said lens frames and said fastening receiving means of said nose portion of said lens holding means to secure said lens supporting frames to said lens holding means to thereby form a unitary eyeglass assembly, dismountable for lens replacement.

6. Eyeglass assembly as defined in claim 5, wherein said nose bridge includes means coupling said free ends of said lens frames; said second fastening receiving means extending through said coupling means and said fastening receiving means.

7. Eyeglass assembly as defined in claim 5, wherein each said lens covering portion has a peripheral rear rim to contain the periphery of said lens.

8. Eyeglass assembly as defined in claim 5, wherein said nose bridge includes an integral U-shaped nose contacting lower extension.

9. Eyeglass assembly as defined in claim 5, wherein each said lens frame includes a temple extension.

10. Eyeglass assembly as defined in claim 9, wherein each said temple extension includes means for receiving a strap for securing said assembly to a wearer's head.

11. Protective eyeglass assembly comprising:

a pair of separate lens supporting frames, each frame defining a C-shaped body having free ends, said free ends defining fastening receiving means;

a pair of lenses each having a peripheral portion bearing against said body;

a pair of separate lens holders; each said lens holder defining a C-shaped body covering part of said lens peripheral portion and part of said lens frame;

first fastening means securing said holders to said frames to tightly hold said lenses therebetween and to form a pair of individual lens assemblies;

a nose bridge defining a pair of fastening receiving means and having opposite lateral portions, each lateral portion extending over an uncovered part of said lens and a part of said lens frame; and second fastening means engaging said fastening means of said free ends of said lens frames and said fastening receiving means of said nose bridge to secure said lens supporting frames to said lens holders to form a unitary eyeglass assembly, dismountable for lens replacement.

12. Eyeglass assembly as defined in claim 11, wherein said nose bridge includes means for coupling with said free ends of said lens frames; said second fastening means extending through said coupling means and said fastening receiving means.

13. Eyeglass assembly as defined in claim 11, wherein said nose bridge includes a U-shaped nose contacting lower extension.

14. Eyeglass assembly as defined in claim 11, wherein each said lens frame includes a temple extension.

15. Eyeglass assembly as defined in claim 14, wherein each said temple extension includes means for receiving a strap for securing said assembly to a wearer's head.

\* \* \* \* \*